US007981890B2

(12) United States Patent
Javaid et al.

(10) Patent No.: US 7,981,890 B2
(45) Date of Patent: Jul. 19, 2011

(54) PHTHALAZINONE DERIVATIVES

(75) Inventors: Muhammad Hashim Javaid, Cambridge (GB); Keith Allan Menear, Cambridge (GB); Niall Morrison Barr Martin, Cambridge (GB)

(73) Assignee: AstraZeneca AB, Sodertalje (SE)

( * ) Notice: Subject to any disclaimer, the term of this patent is extended or adjusted under 35 U.S.C. 154(b) by 33 days.

(21) Appl. No.: 12/209,400

(22) Filed: Sep. 12, 2008

(65) Prior Publication Data
US 2009/0186897 A1 Jul. 23, 2009

Related U.S. Application Data

(60) Provisional application No. 60/972,384, filed on Sep. 14, 2007, provisional application No. 61/032,642, filed on Feb. 29, 2008.

(51) Int. Cl.
*A01N 43/58* (2006.01)
*A01N 43/60* (2006.01)
*A61K 31/495* (2006.01)
*A61K 31/50* (2006.01)
*A61K 31/501* (2006.01)
*C07D 237/30* (2006.01)
*C07D 321/00* (2006.01)

(52) U.S. Cl. ............... 514/248; 514/252.01; 544/237; 548/366.4

(58) Field of Classification Search ............... 514/248, 514/252.01; 544/237; 548/366.4
See application file for complete search history.

(56) References Cited

U.S. PATENT DOCUMENTS

| | | | |
|---|---|---|---|
| 3,813,384 A | 5/1974 | Vogelsang et al. |
| 4,665,181 A | 5/1987 | Thomas et al. |
| 4,841,047 A | 6/1989 | Engel et al. |
| 4,912,115 A | 3/1990 | Bomhard et al. |
| 5,032,617 A | 7/1991 | Lee et al. |
| 5,041,653 A | 8/1991 | Lee et al. |
| 5,215,738 A | 6/1993 | Lee et al. |
| 5,556,856 A | 9/1996 | Engel et al. |
| 5,587,384 A | 12/1996 | Zhang et al. |
| 5,648,355 A | 7/1997 | Theoharides |
| 5,874,444 A | 2/1999 | West |
| 5,886,178 A | 3/1999 | Allen et al. |
| 6,197,785 B1 | 3/2001 | Jackson et al. |
| 6,340,684 B1 | 1/2002 | Napoletano et al. |
| 6,426,415 B1 | 7/2002 | Jackson et al. |
| 6,476,048 B1 | 11/2002 | Szabo et al. |
| 6,498,160 B2 | 12/2002 | Napoletano et al. |
| 6,514,983 B1 | 2/2003 | Li et al. |
| 6,514,984 B1 | 2/2003 | Watanabe |
| 6,635,642 B1 | 10/2003 | Jackson et al. |
| 6,677,333 B1 | 1/2004 | Seko et al. |
| 6,903,098 B1 | 6/2005 | Lubisch et al. |
| 7,041,675 B2 | 5/2006 | Lubisch et al. |
| 7,087,637 B2 | 8/2006 | Grandel et al. |
| 7,151,102 B2 | 12/2006 | Martin et al. |
| 7,196,085 B2 | 3/2007 | Martin et al. |
| 7,402,580 B2 | 7/2008 | Seko et al. |
| 2004/0176361 A1 | 9/2004 | Fujio et al. |
| 2005/0059663 A1 | 3/2005 | Martin et al. |
| 2005/0080096 A1 | 4/2005 | Ishida et al. |
| 2005/0227919 A1 | 10/2005 | Kudos |
| 2006/0063767 A1 | 3/2006 | Javaid et al. |
| 2006/0142293 A1 | 6/2006 | Martin et al. |
| 2007/0093489 A1 | 4/2007 | Javaid et al. |
| 2008/0161280 A1 | 7/2008 | Gandhi et al. |
| 2008/0269234 A1 | 10/2008 | Gandhi et al. |

FOREIGN PATENT DOCUMENTS

| | | |
|---|---|---|
| CA | 972755 | 8/1975 |
| CA | 2352194 | 4/2001 |
| DE | 2143745 | 3/1973 |
| DE | 3813531 | 4/1988 |
| DE | 287 032 | 2/1991 |
| EP | 0030861 | 6/1981 |
| EP | 0269968 | 6/1988 |
| EP | 0355750 | 2/1990 |
| EP | 0389995 | 10/1990 |

(Continued)

OTHER PUBLICATIONS

Affar, E. B. et al., "Immunodot blot method for the detection of poly(ADP-ribose) synthesized in vitro and in vivo," Anal. Biochem 259(2):280-283 (1998).

Al-Dabbagh and Smith, "Species differences in oxidative drug metabolism: some basic considerations." Archives of toxicology, Supplement. Archiv fur Toxikologie. Supplement, vol. 7, 219-231 (1984).

(Continued)

*Primary Examiner* — Jennifer M Kim
*Assistant Examiner* — Paul Zarek
(74) *Attorney, Agent, or Firm* — Morgan, Lewis & Bockius LLP

(57) ABSTRACT

A compound of the formula (I):

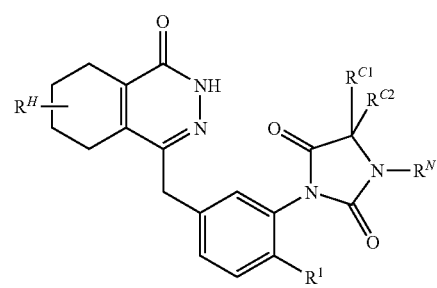

wherein $R^H$ represents one or more optional substituents on the fused cyclohexene ring; $R^1$ is selected from H and halo; $R^N$ is selected from H and optionally substituted $C_{1-10}$ alkyl; and $R^{C1}$ and $R^{C2}$ are independently selected from H, R, C(=O)OR, where R is optionally substituted $C_{1-10}$ alkyl, optionally substituted $C_{5-20}$ aryl or optionally substituted $C_{3-20}$ heterocyclyl; $R^{C1}$ and $R^{C2}$ together with the carbon atom to which they are attached may form an optionally substituted spiro-fused $C_{5-7}$ carbocyclic or heterocyclic ring.

6 Claims, No Drawings

FOREIGN PATENT DOCUMENTS

| | | |
|---|---|---|
| EP | 0502575 | 9/1992 |
| EP | 0590551 | 4/1994 |
| EP | 0634404 | 1/1995 |
| EP | 0699754 | 3/1996 |
| EP | 0705903 | 4/1996 |
| EP | 0792643 | 9/1997 |
| EP | 1908481 | 4/2008 |
| FR | 2262513 | 9/1975 |
| GB | 721286 | 1/1955 |
| GB | 2384776 | 3/2004 |
| IT | MI98A001671 | 4/1999 |
| JP | 54156526 | 12/1979 |
| JP | 58164577 | 9/1983 |
| JP | 62-252774 | 11/1987 |
| WO | WO 91/18591 | 12/1991 |
| WO | WO 93/14086 | 7/1993 |
| WO | WO 94/10151 | 5/1994 |
| WO | WO 95/24379 | 9/1995 |
| WO | WO 96/19225 | 6/1996 |
| WO | WO 98/43477 | 10/1998 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 99/47494 | 9/1999 |
| WO | WO 00/05219 | 2/2000 |
| WO | WO 00/42040 | 7/2000 |
| WO | WO 00/44726 | 8/2000 |
| WO | WO 00/67734 | 11/2000 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 02/36576 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/063874 | 8/2003 |
| WO | WO 03/070707 | 8/2003 |
| WO | WO 03/070726 | 8/2003 |
| WO | WO 03/080581 | 10/2003 |
| WO | WO 03/093261 | 11/2003 |
| WO | WO 2004/080976 | 9/2004 |
| WO | WO 2005/053662 | 6/2005 |
| WO | WO 2006/137510 | 12/2006 |
| WO | WO 2007/045877 | 4/2007 |
| WO | WO 2008/083027 | 7/2008 |

OTHER PUBLICATIONS

Ame, J-C. et al., "PARP-2, a novel mammalian DNA damage-dependent poly(ADP-ribose) polymerase," J. Biol. Chem. 274(25):17860-17868 (1999).
Ame, J-C. et al., "The PARP superfamily," BioEssays 26:882-893 (2004).
Angell, S.M. et al., "Consistent gene silencing in transgenic plants expressing a replicating potato virus X RNA," EMBO J. 16(12):3675-3684 (1997).
Arnaudeau, C. et al., "DNA double-strand breaks associated with replication forks are predominantly repaired by homologous recombination involving an exchange mechanism in mammalian cells," J. Mol. Biol 307:1235-1245 (2001).
Banasik, M. et al., "Inhibitors and activators of ADP-ribosylation reactions," Mol. Cell Biochem. 138:185-197 (1994).
Banasik, M. et al., "Specific Inhibitors of Poly (ADP-Ribose) Synthetase and Mono (ADP-Ribosyl) transferse", J. Biol. Chem., vol. 267, 1569-1575 (1992).
Ben-Hur, E. et al., "Inhibitors of poly (ADP-ribose) synthesis enhance radiation response by differentially affecting repair of potentially lethal versus sublethal damage," Br. J. Cancer 49(VI):39-42 (1984).
Berge et al., "Pharmaceutically Acceptable Salts," J. Pharm. Sci., vol. 66, 1-19. Protective Groups in Organic Synthesis (T. Green and P. Wuts, Wiley, 1991) (1977).
Berger, N. A. et al., "Poly (ADP-ribose) in cellular response to DNA damage", Radiation Research, 101:4-14 (1985).
Bhattacharyya, A. et al., "The breast cancer susceptibility gene BRCA1 is required for subnuclear assembly of Rad51 and survival following treatment with the DNA cross-linking agent cisplatin," J. Biol. Chem. 275(31): 23899-23903 (2000).
Bloch, W. et al., "Poly-adenosine diphosphate-ribose polymerase inhibition for myocardial protection: pathophysiologic and physiologic considerations," J. Thoracic Card. Surg. 128(2):323-324 (2004).
Bold, G. et al., "New anilinophthalazines as potent and orally well absorbed inhibitors of the VEGF receptor tyrosine kinases useful as antagonists of tumor-driven angiogenesis," J. Med. Chem. 43:3200 (Abstract) (2000).
Bold, G. et al., "New anilinophthalazines as potent and orally well absorbed inhibitors of the FEBF receptor tyrosine kinases useful as antagonists of tumour-driven angiogenesis", J. Med. Chem., 43(12):2310-2323 (2000).
Bowman et al., "Differential effects of the poly (ADP-ribose) polymerase (PARP) inhibitor NU 1025 on topoisomerase I and II inhibitor cytotoxicity in L1210 cells in vitro," British Journal of Cancer, 84(1):106-112 (2001).
Brummelkamp, T. R. et al., "A system for stable expression of short interfering RNAs in mammalian cells," Science 296:550-553 (2002).
Bundgaard, H., "Design of prodrugs: Bioreversible derivatives for various functional groups and chemical entities" Design of Prodrugs, Chapter 1 Elsevier Science Publishers (1985).
Burzio, L. et al., "Poly (adenosine diphosphoribose) synthase activity of isolated nuclei of normal and leukemic leukocytes (38930)", Proc. Soc. Exp. Bio. Med., 149:933-938 (1975).
Calabrese, C.R. et al., "Identification of potent nontoxic poly(ADP-ribose) polymerase-1 inhibitors: chemopotentiation and pharmacological studies," Clin. Can. Res. 9:2711-2718 (2003).
Caldecott, K.W., "DNA single-strand break repair and spinocerebellar ataxia," Cell 112:7-10 (2003).
Cantoni, O. et al., "Hydrogen peroxide insult in cultured mammalian cells: relationships between DNA single-strand breakage, poly (ADP-ribose) metabolism and cell killing", Biochim. Biophys. Acta, 1014:1-7 (1989).
Catteau, A. et al., "Methylation of the BRCA1 promoter region in sporadic breast and ovarian cancer: correlation with disease characteristics," Oncogene 18:1957-1965 (1999).
Chalmers, A.J. , "Poly(ADP-ribose) polymerase-1 and ionizing radiation: sensor, signaller and therapeutic target," Clin. Onc. 16:29-39 (2004).
Chappuis, P. O. et al., "Risk Assessment and Genetic Testing," Cancer Treat. Res., 107:29-59 (2002).
Chiarugi, A., "Poly(ADP-ribose) polymerase: killer or conspirator? The 'suicide hypothesis' revisted," Trends in Pharm. Sci. 23(3):122-129 (2002).
Cockcroft, X-L. et al., "Phthalazinones 2: optimisation and synthesis of novel potent inhibitors of poly(ADP-ribose)polymerase," Biorg. Med. Chem. Lett. 16:1040-1044 (2006).
Cosi, C. et al., "Poly (ADP-ribose) polymerase: early involvement in glutamate-induced neurotoxicity in cultured cerebellar granule cells", J.Neurosci. Res., 39:38-46 (1994).
Cosi, C., "New inhibitors of poly(ADP-ribose) polymerase and their potential therapeutic targets," Expert Opin. Ther. Patents 12(7): 1047-1071 (2002).
Couzin, J., "The twists and turns in BRCA's path," Science 302:591-592 (2003).
Crooke, S.T., "Therapeutic applications of oligonucleotides," Ann. Rev. Pharmacol. Toxicol. 32:329-376 (1992).

Cuzzocrea, S., "Shock, inflammation and PARP," Pharmacological Res. 52:72-82 (2005).
D'Adda Di Fagagna, F. et al., "Functions of poly(ADP-ribose) polymerase in controlling telomere length and chromosomal stability", Nature Gen., 23(1): 76-80 (1999).
D'Amours, D. et al., "Poly(ADP-ribosyl)ation reactions in the regulation of nuclear functions", Biochem. J., 342:249-268 (1999).
D'Amours, D. et al., "The MRE11 complex: at the crossroads of DNA repair and checkpoint signalling," Mol. Cell Biol. 3:317-327 (2002).
D'Andrea, A. D. et al., "The fanconi anaemia/BRCA pathway," Nat. Rev. Cancer 3:23-34 (2003).
Dantzer, F. et al., "Base excision repair is imparied in mammalian cells lacking poly(ADP-ribose) polymerase-1," Biochemistry 39:7559-7569 (2000).
Dantzer, F. et al., "Involvement of poly(ADP-ribose) polymerase in base excision repair," Biochimie 81:69-75 (1999).
Davies, A. A. et al., "Role of BRCA2 in control of the RAD51 recombination and DNA repair protein," Mol. Cell 7:273-282 (2001).
Dillon, K. J. et al., "A flashplate assay for the idenfification of PARP-1 inhibitors," J. Biomolecular Screening 8(3):347-352 (2003).
Durkacz, B. W. et al., "(ADP-ribose)n participates in DNA excision repair", Nature, 283(7):593-596 (1980).
Dusemund, "Isochino [3,2-a]phthalazin-5,8-dione", Arch. Pharm., (Weinhein) 925-930 (English Abstract) (1982).
Dusemund, J., "Einfache synthese von isochino[2,3-c][2,3]benzoxazepinon und -[2,3]benzodiazepinonen sowie ihrer vorstufen," Arch. Pharm. 321:41-44 (1988).
Egawa, C. et al., "Decreased expression of BRCA2 mRNA predicts favorable response to docetaxel in breast cancer," Int. J. Cancer 95:255-259 (2001).
Egawa, C. et al., "Quantitative analysis of estrogen receptor-? and -? messenger RNA expression in normal and malignant thyroid tissues by real-time polymerase chain reaction," Oncology 61:293-298 (2001).
Ehrlich, H.A. et al., "Recent advances in the polymerase chain reaction," Science 252:1643-1650 (1991).
Elbashir, S. M. et al., "Duplexes of 21-nucleotide RNAs mediate RNA interference in cultured mammalian cells," Nature 411:494-498 (2001).
El-Tamaty et al., Synthesis and biological activity of some 4-benzyl-1(2H)-phthalazinone derivatives, Indian J. Chemistry, v. 35B, 1067-1072 (1996).
El-Tamaty, E-S.H. et al., "Synthesis and biological activity of some 4-benzyl-1(2H)-phthalazinone derivatives," Chem. Abs. 125:23, 125:300924j (1996).
Esteller, M. et al., "Promoter hypermethylation and BRCA1 inactivation in sporadic breast and ovarian tumors," J. Natl. Cancer Inst. 92(7):564-569 (2000).
Ferraris, D. et al., "Design and synthesis of poly ADP-ribose polymerase-1 inhibitors. 2. Biological evaluation of Aza-5[H]-phenanthridin-6-ones as potent, aqueous-soluble compounds for the treatment of ischemic injuries," J. Med. Chem. 46:3138-3151 (2003).
Fire, A. et al., "Potent and specific genetic interference by double-stranded RNA in Caenorhabditis elegans," Nature 391:806-811 (1998).
Foray, N. et al., "A subset of ATM- and ATR-dependent phosphorylation events requires the BRCA1 protein," Embo J. 22(11):2860-2871 (2003).
Fujisawa Pharmaceutical Co., "Preaparation of 2-carboxyalkyl-4-aralkylphthalazine derivatives as aldose reductase inhibitors and a process for preparing them," Chemical Abstracts 109:6531 (1987).
Fuska, J. et al., "New Cytotoxic and antitumor agents," Chemical Abstracts, 104:102050 (1985).
Gaken, J. A. et al., "Efficient retroviral infection of mammalian cells is blocked by inhibition of poly(ADP-ribose) polymerase activity", J. Virology, 70(6): 3992-4000 (1996).
Greene, T.W. et al., Protective Groups in Organic Synthesis, Chapters 2 and 7, John Wiley & Sons Inc. 17-23 and 494-503 (1999).
Griffin et al., "The role of inhibitors of poly (ADP-ribose) polymerase as resistance-modifying agents in cancer therapy," Biochimie 77:408-422 (1995).
Griffin, C.S. et al., "Mammalian recombination-repair genes XRCC2 and XRCC3 promote correct chromosome segregation," Nature Cell Biol. 2:757-761 (2000).
Grube, K. et al., "Direct stimulation of poly(ADP ribose) polymerase in permeabilized cells by double-stranded DNA eligomers," Anal. Biochem. 193:236-239 (1991).
Haber, J. E., "DNA recombination: the replication connection," Trends Biochem. Sci. 24:271-275 (1999).
Hall, I.H. et al., "Cytotoxicity of imides-N-alkyl semicarbazones, thiosemicarbazones, acetylhydrazones and related derivatives," Anti-Cancer Drugs (and abstract 122:204573), V.6, 147-153 (1995).
Halldorsson, H. et al., "Poly(ADP-ribose) polymerase activity in nucleotide permeable cells," FEBS Lett. 85(2):349-352 (1978).
Hawley's Condensed Chemical Dictionary, 13th ed., Van Nostrand Reinhold eds. 716 and 825 (1997).
Herceg, Z. et al., "Functions of poly(ADP-ribose) polymerase (PARP) in DNA repair, genomic intergrity and cell death," Mut. Res. 477:97-110 (2001).
Hirai, K. et al., "Aberration of poly(adenosine diphosphate-ribose) metabolism in human colon adenomatous polyps and cancers", Cancer Res., 43:3441-3446 (1983).
Hiramoto, T. et al., "Mutations of a novel human RAD54 homologue, RAD54B, in primary cancer," Oncogene 18:3422-3426 (1999).
Hoeijmakers, J. H.J., "Genome maintenance mechanisms for preventing cancer," Nature 411:366-374 (2001).
Hughes-Davies, L. et al., "EMSY links the BRCA2 pathway to sporadic breast and ovarian cancer," Cell 115:523-535 (2003).
Islam, A.M. et al., "4, 5, 6, 7-Tetraiodo-3-benzalphthalides and related compounds," (1981) Chemical Abstracts 95:187182.
Islam, A.M. et al., "Action of phosphorus pentasulfide on the products of interaction of p-sulfamoylphenylacetic acids with phthalic anhydride," Chemical Abstracts 95:62106 (1981).
Islam, A.M. et al., "Thioarylidenephthalides and related compounds: Part II. Reactions with amino compounds," Chemical Abstracts 87:67943 (1977).
Jackson, S.P., "Sensing and repairing DNA double-strand breaks," Carcinogenesis 23(5):687-696 (2002).
Janatova, M. et al., "Detection of the most frequent mutations in BRCA1 gene on polyacrylamide gels containing spreadex polymer NAB," Neoplasma 50(4):246-250 (2003).
Jancarkova, N., "Detection and incidence of mutations of BRCA1 gene in patients with cancer of the breast and ovary," Ceska Gynekol. 68(1):11-16 (2003).
Jantzen et al., "B. Prodrugs" taken from Modern Pharmaceutics, Third Edition, Banker and Rhodes, editors p. 596 (1996).
Jasin, M., "Homologous repair of DNA damage and tumorigenesis: the BRCA connecton," Oncogene 21(58):8981-8993 (2002).
Jijon, H.B. et al., "Inhibition of poly(ADP-ribose) polymerase attenuates inflammation in a model of chronic colitis," Am. J. Physiol. Gastrointest. Liver Physiol. 279:G641-G651 (2000).
Johnson, R.D. et al., "Mammalian XRCC2 promotes the repair of DNA double-strand breaks by homologous recombination," Nature 401:397-399 (1999).
Kanaar, R. et al., "Molecular mechanisms of DNA double-strand break repair," Trends Cell Biol. 8:483-489 (1998).
Kashani-Sabet, M. et al., "Application of ribozymes to cancer gene therapy," Cancer Gene Therapy 2(3):213-223 (1995).
Kawamura, I. et al., "Ponalrestat, an aldose reductase inhibitor," Chemical Abstract 132:273943 (1999).
Kerr, P. et al., "New complexities for BRCA1 and BRCA2," Curr. Biol. 11:R668-676 (2001).
Kerrigan, F. et al. "Imide-substituted 4-benzyl-2H-phthalazin-1 ones: potent inhibitors of poly(ADP-ribose) polymerase-1 (PARP-1)," Poster at 12th SCI-RSC Medicinal Chemistry Symposium, Cambridge, 7-10 (2003).
Khanna, K. K. et al., "DNA double-strand breaks: signaling, repair and the cancer connection," Nat. Genet. 27(3):247-254 (2001).
Kraakman-Van Der Zwet, M. et al., "Brca2 (XRCC11) deficiency results in radioresistant DNA synthesis and a higher frequency of spontaneous deletions," Mol. Cell Biol. 22(2):669-679 (2002).
Kuperstein, G. et al., "A rapid fluorescent multiplexed-PCR analysis (FMPA) for founder mutations in the BRCA1 and BRCA2 genes," Clin. Genet. 57:213-220 (2000).

Kupper, J-H. et al., "Trans-dominant inhibition of poly(ADP-ribosyl)ation potentiates carcinogen-induced gene amplification in SV40-transformed Chinese hamster cells," Cancer Res. 56:2715-2717 (1996).

Lakhani, S. R. et al., "The pathology of familial breast cancer: predictive value of immunohistochemical markers estrogen receptor, progesterone receptor, HER-2, and p53 in patients with mutations in BRCA1 and BRCA2," J. Clin. Oncol. 20(9):2310-2318 (2002).

Le Rhun, Y. et al., "Cellular responses to DNA damage in the absence of poly(ADP-ribose)polymerase", Biochem. Biophys. Res. Commun., 245:1-10 (1998).

Lemay, M. et al., "Detection of DNA damage and identification of UV-induced photoproducts using the cometassay kit," Biotechniques 27:846-851 (1999).

Liaudet, L. et al., "Protection against hemorrhagic shock in mice genetically deficient in poly(ADP-ribose)polymerase", Proc. Natl. Acad. Sci. U.S.A., 97(3):10203-10208 (2000).

Lindahl, T. et al, "Post-translational modification of poly(ADP-ribose) polymerase induced by DNA strand breaks," TIBS 20:405-411 (1995).

Lindahl, T. et al, "Quality control by DNA repair," Science 286:1897-1905 (1999).

Loh, V.M. et al., "Phthalazinones. Part 1: The design and synthesis of a novel series of potent inhibitors of poly(ADP-ribose)polymerase," Bioorg. Med. Chem. Lett. 15:2235-2238 (2005).

Lundin, C. et al., "Different roles for nonhomologous end joining and homologous recombination following replication arrest in mammalian cells," Mol. Cell. Biol. (2002) 22(16):5869-5878.

Lundin, C. et al., "RAD51 is involved in repair of damage associated with DNA replication in mammalian cells," J. Mol. Biol. 328:521-535 (2003).

Magnusson, J. et al., "Inhibitor of poly(ADP-ribose)transferase potentiates the recombinogenic but not the mutagenic action of alkylating agents in somatic cells in vivo in drosophila melanogaster," Mutagenesis 5(5):511-514 (1990).

Martin, N. et al., "DNA repair inhibition and cancer therapy," J. Photochem. and PhotoBiol. B: Biology 63:162-170 (2001).

Martin, N. et al., "Phthalazinone derivatives as potent PARP-1 inhibitors", 13th Intl. Symposium on ADP-ribosylation, Abstract 107 (2001).

Matsuda, M. et al., "Mutations in the RAD54 recombination gene in primary cancers," Oncogene 18:3427-3430 (1999).

McNealy, T. et al., "Intrinsic presence of poly (ADP-ribose) is significantly increased in malignant prostate compared to benign prostate cell lines," Anticancer Res. 23:1473-1478 (2003).

Menissier De Murcia, J. et al., "Functional interaction between PARP-1 and PARP-2 in chromosome stability and embryonic development in mouse," EMBO J. 22(9):2255-2263 (2003).

Menissier De Murcia, J. et al., "Requirement of poly(ADP-ribose)polymerase in recovery from DNA damage in mice and cells", Proc. Natl. Acad. Sci. U.S.A., 94:7303-7307 (1997).

Mercola, D. et al., "Antisense approaches to cancer gene therapy," Cancer Gene Therapy 2(1):47-59 (1995).

Miller, B.A., "Inhibition of TRPM2 function by PARP inhibitors protects cells from oxidative stress-induced death," Br. J. Pharmacology 143:515-516 (2004).

Miwa, M. et al., "Cell density-dependent increase in chromatin-associated ADP-ribosyltransferase activity in simian virus 40-transformed cells", Arch. Biochem. Biophys., 181:313-321 1977.

Morrison, C. et al., "Genetic interaction between PARP and DNA-PK in V(D)J recombination and tumorigenesis," Nature Genetics 17:479-482 (1997).

Moynahan, M. E. et al., "Brca1 controls homology-directed DNA repair," Mol. Cell 4:511-518 (1999).

Moynahan, M. E. et al., "BRCA2 is required for homology-directed repair or chromosomal breaks," Mol. Cell 7:263-272 (2001).

Mullis, K. et al., "Specific enzymatic amplification of DNA in vitro: the polymerase chain reaction," Cold Spring Harbor Symp. Quant. Biol. 51:263-273 (1987).

Nakamura, J. et al., "Quantitation of intracellular NAD(P)H can monitor an imbalance of DNA single strand break repair in base excision repair deficient cells in real time," Nuc. Acids Res. 31(17):e104 1-7 (2003).

Nathanson, K. L. et al., "Breast cancer genetics: what we know and what we need," Nat. Med. 7(5):552-556 (2001).

Neuhausen, S. L. et al., "Mutation testing of early-onset breast cancer genes BRCA1 and BRCA2," Genet. Test 1(2):75-83 (1997).

Noel, G. et al., "Poly(ADP-ribse) polymerase (PARP-1) is not involved in DNA double-strand break recovery," BMC Cell Biol. 4:7-17 (2003).

Pacher et al., "The Role of Poly(ADP-Ribose) Polymerase Activation in the Development of Myocardial and Endothelial Dysfunction in Diabetes," Diabetes, 51:514-521 (2002).

Perkins, E. et al., "Novel inhibitors of poly(ADP-ribose)polymerase/PARP1 and PARP2 identified using a cell-based screen in yeast", Cancer Res., vol. 61, 4175-4183 (2001).

Pierce, A.J. et al., "XRCC3 promotes homology-directed repair of DNA damage in mammalian cells," Genes & Dev. 13:2633-2638 (1999).

Radice, P. J., "Mutations of BRCA genes in hereditary breast and ovarian cancer," Exp. Clin. Cancer Res. 21(3 Suppl.):9-12 (2002).

Rattan, S. I. et al., "Kinetin delays the onset of ageing characteristics in human fibroblasts", Biochem. Biophys. Res. Commun., 201(2):665-672 (1994).

Said, S. I. et al., "Excitotoxicity in the lung: N-methy-D-aspartate-induced, nitric oxide-dependent, pulmonary edema is attenuated by vasoactive intestinal peptide and by inhibitors of poly(ADP-ribose)polymerase", Proc. Natl. Acad. Sci. U.S.A., 93:4688-4692 (1996).

Samper, E. et al., "Normal telomere length and chromosomal end capping in poly(ADP-ribose) polymerase-deficient mice and primary cells despite increased chromosomal instability," J. Cell Biol. 154(1):49-60 (2001).

Satoh, M.S. et al., "Role of poly(ADP-ribose) formation in DNA repair," Nature 356:356-358 (1992).

Schlicker, A. et al., "4-Amino-1,8-napthalimide: a novel inhibitor of poly(ADP-ribose)polymerase and radiation sensitizer", Int. J. Radiat. Bio., 75(1):91-100 (1999).

Schreiber, V. et al., "A dominant-negative mutant of human poly(ADP-ribose) polymerase affects cell recovery, apoptosis, and sister chromatid exchange following DNA damage," Proc. Natl. Acad. Sci. USA 92:4753-4757 (1995).

Schreiber, V. et al., "Poly(ADP-ribose) polymerase-2 (PARP-2) is required for efficient base excision DNA repair in association with PARP-1 and XRCC1," J. Biol. Chem. 277(25):23028-23036 (2002).

Schultz, N. et al., "Poly(ADP-ribose) polymerase (PARP-1) has a controlling role in homologous recombination," Nucleic Acids Res. 31:4959-4964 (2003).

Semionov, A. et al., "Inhibition of poly(ADP-ribose)polymerase stimulates extrachromosomal homologous recombination in mouse Ltk-fibroblasts," Nuc. Acids Res. 27(22):4526-4531 (1999).

Shah, G.M. et al., "Complete inhibition of poly(ADP-ribose) polymerase activity prevents the recovery of C3H10T1/2 cells from oxidative stress," Biochimica et Biophysica Acta 1312:1-7 (1996).

Shall, S. et al., "Poly(ADP-ribose) polymerase-1: what have we learned from the deficient mouse model?" Mutat. Res. 460:1-15 (2000).

Shimizu, T. et al., "Inhibitory effects of azelastine and tranilast on leukotriene B4 and leukotriene C4 generation by rat colonic mucosa", Prostaglandins Leukotrienes and Essential Fatty Acids, 53:355-358 (1995).

Silverman, R.B., "Chapter 8. Prodrugs and drug delivery system" The Organic Chemistry of Drug Design and Drug Action, 352-400 Academic Press, Inc. (1992).

Simbulan-Rosenthal, C.M. et al., "Chromosomal aberrations in PARP-/-mice: genome stabilization in immortalized cells by reintroduction of poly(ADP-ribose) polymerase cDNA," Proc. Natl. Acad. Sci. USA 96(23):13191-13196 (1999).

Skehan, P. et al., "New colorimetric cytotoxicity assay for anticancer-drug screening", J. Natl. Cancer Inst., 82(13):1107-1112 (1990).

Southan, G.J. and Szabo, C., "Poly (ADP-ribose) polymerase inhibitors," Current Medicinal Chemistry, 10(4): 321-340 (2003).

Suto, M.J. et al., "Dihydroisoquinolinones: the design and synthesis of a new series of potent inhibitors of poly(ADP-ribose) polymerase," Anticancer Drug Des. 7:107-117 (1991).

Szabo, "9. Role of poly(ADP-ribose) polymerase activation in the pathogenesis of shock and inflammation" PARP as a Therapeutic Target, Zhang, Ed. CRC Press 169-204 (2002).

Szabo, C. et al., "Endothelial dysfunction in a rat model of endotoxic shock", J. Clin. Invest., 100, 723-25 (1997).

Szabo, G. et al., "Poly-ADP-ribose polymerase inhibition protects against myocardial and endothelial reperfusion injury after hypothermic cardiac arrest," J. Thoracic Cardiovas. Surg. 126(3):651-658 (2003).

Taniguchi, T. et al., "Disruption of the Fanconi anemia-BRCA pathway in cisplatin-sensitive ovarian tumors," Nat. Med. 9(5):568-574 (2003).

Tarsounas, M. et al., "BRCA2-dependent and independent formation of RAD51 nuclear foci," Oncogene 22:1115-1123 (2003).

Tasatargil, A. et al., "Poly(ADP-ribose) polymerase inhibition prevents homocysteine-induced endothelial dysfunction in the isolated rat aorta," Pharmacology 72:99-105 (2004).

Tebbs, R.S. et al., "Correction of chromosomal instability and sensitivity to diverse mutagens by a cloned cDNA of the XRCC3 DNA repair gene," Proc. Natl. Acad. Sci. USA 92:6354-6358 (1995).

Tentori, L. et al., "Potential clinical applications of poly(ADP-ribose) polymerase (PARP) inhibitors," Pharm. Res. 45(2):73-85 (2002).

Thompson, L. H. et al., "Recombinational DNA repair and human disease," Mutat. Res. 509:49-78 (2002).

Tracey, W. et al., "Aldose reductase inhibition alone or combined with an adenosine A3 agonist reduces ischemic myocardial injury," Chemical Abstract 134:65983 (2000).

Tutt, A N.J. et al., "Disruption of Brca2 increases the spontaneous mutation rate in vivo: synergism with ionizing radiation," Embo Reports 3(3):255-260 (2002).

Tutt, A. et al., "Mutation in Brca2 stimulates error-prone homology-directed repair of DNA double-strand breaks occurring between repeated sequences," EMBO J. 20(17):4704-4716 (2001).

Tutt, A. et al., "The relationship between the roles of BRCA genes in DNA repair and cancer predisposition," Trends Mol. Med. 8(12):571-576 (2002).

Uhlmann, E. et al., Antisense oligonucleotides: a new therapeutic principle, Chem. Rev. 90(4):543-584 (1990).

Van Gent, D.C. et al., "Chromosomal stability and the DNA double-stranded break connection," Nature Reviews 2:196-206 (2001).

Venkitaraman, A. R., "Cancer susceptibility and the functions of BRCA1 and BRCA2," Cell 108:171-182 (2002).

Vippagunta, S.R. et al., "Crystalline solids," Adv. Drug Delivery Reviews 48:3-26 (2001).

Virag and Szabo, "The Therapeutic Potential of Poly(ADP-Ribose) Polymerase Inhibitors," Pharmacological Reviews, 54(3):375-429 (2002).

Voinnet, O. et al. "Systemic signalling in gene silencing," Nature 389:553 (1997).

Waldman, A.S. et al., "Stimulation of intrachromosomal homologous recombination in mammalian cells by an inhibitor of poly(ADP-ribosylation)," Nuc. Acids Res. 19(21):5943-5947 (1991).

Wang, Z.-Q. et al., "Mice lacking ADPRT and poly(ADP-ribosyl)ation develop normally but are susceptible to skin disease", Genes Dev., 9:509-520 (1995).

Wang, Z.-Q. et al., "PARP is important for genomic stability but dispensable in apoptosis," Genes Dev. 11:2347-2358 (1997).

West, A.R. "Solid State Chemistry and its Applications" Wiley, New York, 358 and 365 (1988).

Wood, R.D. et al., "Human DNA repair genes," Science 291:1284-1289 (2001).

Yamaguchi, M. et al., "Novel antiasthmatic agents with dual activities of thromboxane A2 synthetase inhibition and bronchodilation. 1. 2-[2-(1-Imidazolyl)alkyl]-1(2H)-phthalazinones", J. Med. Chem., 36(25):4052-4060 (1993).

Yamaguchi, M. et al., "Novel antiasthmatic agents with dual activities of thromboxane A2 synthetase inhibition and bronchodilation. 2. 4-(3-Pyridyl)-1(2H)-phthalazinones", J. Med. Chem., , vol. 36, No. 25, 4061-4068 (1993).

Zamore, P. D., "RNA interference: listening to the sound of silence," Nature Structural Biology 8(9):746-750 (2001).

Zamore, P. D., "RNAi: double-stranded RNA directs the ATP-dependent cleavage of mRNA at 21 to 23 nucleotide intervals," Cell 101:25-33 (2000).

Zhang, J. et al., "Neuroprotective effects of poly(ADP-ribose) polymerase inhibition on focal cerebral ischemia," Portland Press Proc. 15:125 (1998).

Zhong, Q. et al., "Association of BRCA1 with the hRad50-hMre11-p95 complex and the DNA damage response," Science 285:747-750 (1999).

Zingarelli, B. et al., "Activator protein-1 signalling pathway and apoptosis are modulated by poly(ADP-ribose) polymerase-1 in experimental colitis," Immunology 113:509-517 (2004).

PHTHALAZINONE DERIVATIVES

This application claims the benefit under 35 U.S.C. §119 (e) of U.S. Provisional Application No. 60/972,384 (filed Sep. 14, 2007) and U.S. Provisional Application No. 61/032,642 (filed Feb. 29, 2008), both of which are hereby incorporated by reference in their entirety.

The present invention relates to phthalazinone derivatives and their use as pharmaceuticals. In particular, the present invention relates to the use of these compounds to inhibit the activity of the enzyme poly(ADP-ribose)polymerase-1, also known as poly(ADP-ribose)synthase and poly ADP-ribosyltransferase, and commonly referred to as PARP-1.

The mammalian enzyme PARP-1 (a 113-kDa multidomain protein) has been implicated in the signalling of DNA damage through its ability to recognize and rapidly bind to DNA single or double strand breaks (D'Amours, et al., *Biochem. J.*, 342, 249-268 (1999)).

The family of Poly(ADP-ribose) polymerases now includes around 18 proteins, that all display a certain level of homology in their catalytic domain but differ in their cellular functions (Ame et al., *Bioessays.*, 26(8), 882-893 (2004)). Of this family PARP-1 (the founding member) and PARP-2 are so far the sole enzymes whose catalytic activity are stimulated by the occurrence of DNA strand breaks, making them unique in the family.

It is now known that PARP-1 participates in a variety of DNA-related functions including gene amplification, cell division, differentiation, apoptosis, DNA base excision repair as well as effects on telomere length and chromosome stability (d'Adda di Fagagna, et al., *Nature Gen.*, 23(1), 76-80 (1999)).

Studies on the mechanism by which PARP-1 modulates DNA repair and other processes has identified its importance in the formation of poly(ADP-ribose) chains within the cellular nucleus (Althaus, F. R. and Richter, C., ADP-Ribosylation of Proteins: Enzymology and Biological Significance, Springer-Verlag, Berlin (1987)). The DNA-bound, activated PARP-1 utilizes $NAD^+$ to synthesize poly(ADP-ribose) on a variety of nuclear target proteins, including topoisomerases, histones and PARP itself (Rhun, et al., *Biochem. Biophys. Res. Commun.*, 245, 1-10 (1998))

Poly(ADP-ribosyl)ation has also been associated with malignant transformation. For example, PARP-1 activity is higher in the isolated nuclei of SV40-transformed fibroblasts, while both leukaemic and colon cancer cells show higher enzyme activity than the equivalent normal leukocytes and colon mucosa (Miwa, et al., *Arch. Biochem. Biophys.*, 181, 313-321 (1977); Burzio, et al., *Proc. Soc. Exp. Biol. Med.*, 149, 933-938 (1975); and Hirai, et al., *Cancer Res.*, 43, 3441-3446 (1983)). More recently in malignant prostate tumours compared to benign prostate cells significantly increased levels of active PARP (predominantly PARP-1) have been identified associated with higher levels of genetic instability (McNealy, et al., *Anticancer Res.*, 23, 1473-1478 (2003)).

A number of low-molecular-weight inhibitors of PARP-1 have been used to elucidate the functional role of poly(ADP-ribosyl)ation in DNA repair. In cells treated with alkylating agents, the inhibition of PARP leads to a marked increase in DNA-strand breakage and cell killing (Durkacz, et al., *Nature*, 283, 593-596 (1980); Berger, N. A., *Radiation Research*, 101, 4-14 (1985)).

Subsequently, such inhibitors have been shown to enhance the effects of radiation response by suppressing the repair of potentially lethal damage (Ben-Hur, et al., *British Journal of Cancer*, 49 (Suppl. VI), 34-42 (1984); Schlicker, et al., *Int. J. Radiat. Bioi.*, 75, 91-100 (1999)). PARP inhibitors have been reported to be effective in radio sensitising hypoxic tumour cells (U.S. Pat. No. 5,032,617; U.S. Pat. No. 5,215,738 and U.S. Pat. No. 5,041,653). In certain tumour cell lines, chemical inhibition of PARP-1 (and PARP-2) activity is also associated with marked sensitisation to very low doses of radiation (Chalmers, *Clin. Oncol.*, 16(1), 29-39 (2004))

Furthermore, PARP-1 knockout (PARP –/–) animals exhibit genomic instability in response to alkylating agents and γ-irradiation (Wang, et al., *Genes Dev.*, 9, 509-520 (1995); Menissier de Murcia, et al., *Proc. Natl. Acad. Sci. USA*, 94, 7303-7307 (1997)). More recent data indicates that PARP-1 and PARP-2 possess both overlapping and non-redundant functions in the maintenance of genomic stability, making them both interesting targets (Menissier de Murcia, et al., *EMBO. J.*, 22(9), 2255-2263 (2003)).

PARP inhibition has also recently been reported to have antiangiogenic effects. Where dose dependent reductions of VEGF and basic-fibroblast growth factor (bFGF)-induced proliferation, migration and tube formation in HUVECS has been reported (Rajesh, et al., *Biochem. Biophys. Res. Comm.*, 350, 1056-1062 (2006)).

A role for PARP-1 has also been demonstrated in certain vascular diseases, septic shock, ischaemic injury and neurotoxicity (Cantoni, et al., *Biochim. Biophys. Acta*, 1014, 1-7 (1989); Szabo, et al., *J. Clin. Invest.*, 100, 723-735 (1997)). Oxygen radical DNA damage that leads to strand breaks in DNA, which are subsequently recognised by PARP-1, is a major contributing factor to such disease states as shown by PARP-1 inhibitor studies (Cosi, et al., *J. Neurosci. Res.*, 39, 38-46 (1994); Said, et al., *Proc. Natl. Acad. Sci. U.S.A.*, 93, 4688-4692 (1996)). More recently, PARP has been demonstrated to play a role in the pathogenesis of haemorrhagic shock (Liaudet, et al., *Proc. Natl. Acad. Sci. U.S.A.*, 97(3), 10203-10208 (2000)), eye (Occular) related oxidative damage as in Macular Degeneration (AMD) and retinitis pigmentosis (Paquet-Durand et al., *J. Neuroscience*, 27(38), 10311-10319 (2007), as well as in transplant rejection of organs like lung, heart and kidney (O'Valle, et al., *Transplant. Proc.*, 39(7), 2099-2101 (2007). Moreover, treatment with PARP inhibitors has been shown to attenuate acute diseases like pancreatitis and it associated liver and lung damage caused by mechanisms where PARP plays a role (Mota, et al., *Br. J. Pharmacol.*, 151(7), 998-1005 (2007).

It has also been demonstrated that efficient retroviral infection of mammalian cells is blocked by the inhibition of PARP-1 activity. Such inhibition of recombinant retroviral vector infections was shown to occur in various different cell types (Gaken, et al., *J. Virology*, 70(6), 3992-4000 (1996)). Inhibitors of PARP-1 have thus been developed for the use in anti-viral therapies and in cancer treatment (WO 91/18591).

Moreover, PARP-1 inhibition has been speculated to delay the onset of aging characteristics in human fibroblasts (Rattan and Clark, *Biochem. Biophys. Res. Comm.*, 201(2), 665-672 (1994)) and age related diseases such as atherosclerosis (Hans, et al., *Cardiovasc. Res.*, (Jan. 31, 2008)). This may be related to the role that PARP plays in controlling telomere function (d'Adda di Fagagna, et al., *Nature Gen.*, 23(1), 76-80 (1999)).

PARP inhibitors are also thought to be relevant to the treatment of inflammatory bowel disease (Szabo C., Role of Poly(ADP-Ribose) Polymerase Activation in the Pathogenesis of Shock and Inflammation, In PARP as a Therapeutic Target; Ed J. Zhang, 2002 by CRC Press; 169-204), ulcerative colitis (Zingarelli, B, et al., *Immunology*, 113(4), 509-517 (2004)) and Crohn's disease (Jijon, H. B., et al., *Am. J. Physiol. Gastrointest. Liver Physiol.*, 279, G641-G651 (2000).

Some of the present inventors have previously described (WO 2007/045877) a class of 1(2H)-phthalazinone compounds which act as PARP inhibitors. Some of the compounds can be represented by the formula:

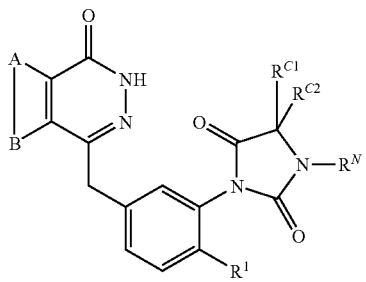

wherein:
A and B together represent an optionally substituted, fused aromatic ring;
$R^1$ is selected from H and halo;
$R^N$ is selected from H and optionally substituted $C_{1-10}$ alkyl;
$R^{C1}$ and $R^{C2}$ are independently selected from H, R, C(=O)OR, where R is optionally substituted $C_{1-10}$ alkyl, optionally substituted $C_{5-20}$ aryl or optionally substituted $C_{3-20}$ heterocyclyl; $R^{C1}$ and $R^{C2}$ together with the carbon atom to which they are attached may form an optionally substituted spiro-fused $C_{5-7}$ carbocyclic or heterocyclic ring.

The present inventors have now discovered that compounds where the fused aromatic ring represented by -A-B— is replaced by a fused cyclohexene ring, the compounds exhibit a surprising increase in the level of inhibition of the activity of PARP, and/or of potentiation of tumour cells to radiotherapy and various chemotherapies, and/or a surprising increase in the solubility of the compound (in aqueous media and/or phosphate buffer solution)—enhanced solubility may be of use in formulation the compounds for administration by an IV route, or for oral formulations (e.g. liquid and small tablet forms) for paediatric use. The oral bioavailablity of the compounds of the present invention may be enhanced.

Accordingly, the first aspect of the present invention provides a compound of the formula (I):

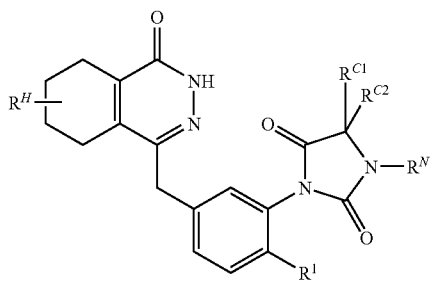

(or a salt, solvate, protected form or prodrug thereof) wherein:
$R^H$ represents one or more optional substituents on the fused cyclohexene ring;
$R^1$ is selected from H and halo;
$R^N$ is selected from H and optionally substituted $C_{1-10}$ alkyl; and
$R^{C1}$ and $R^{C2}$ are independently selected from H, R, C(=O)OR, where R is optionally substituted $C_{1-10}$ alkyl, optionally substituted $C_{5-20}$ aryl or optionally substituted $C_{3-20}$ heterocyclyl; $R^{C1}$ and $R^{C2}$ together with the carbon atom to which they are attached may form an optionally substituted spiro-fused $C_{5-7}$ carbocyclic or heterocyclic ring.

A second aspect of the present invention provides a pharmaceutical composition comprising a compound of the first aspect and a pharmaceutically acceptable carrier or diluent.

A third aspect of the present invention provides the use of a compound of the first aspect in a method of treatment of the human or animal body.

A fourth aspect of the present invention provides the use of a compound as defined in the first aspect of the invention in the preparation of a medicament for:
(a) preventing poly(ADP-ribose) chain formation by inhibiting the activity of cellular PARP (PARP-1 and/or PARP-2);
(b) the treatment of: vascular disease; septic shock; ischaemic injury, both cerebral and cardiovascular; reperfusion injury, both cerebral and cardiovascular; neurotoxicity, including acute and chronic treatments for stroke and Parkinson's disease; haemorraghic shock; eye related oxidative damage; transplant rejection; inflammatory diseases, such as arthritis, inflammatory bowel disease, ulcerative colitis and Crohn's disease; multiple sclerosis; secondary effects of diabetes; as well as the acute treatment of cytoxicity following cardiovascular surgery; pancreatitis; atherosclerosis; or diseases ameliorated by the inhibition of the activity of PARP;
(c) use as an adjunct in cancer therapy or for potentiating tumour cells for treatment with ionizing radiation or chemotherapeutic agents.

In particular, compounds as defined in the first aspect of the invention can be used in anti-cancer combination therapies (or as adjuncts) along with alkylating agents, such as methyl methanesulfonate (MMS), temozolomide and dacarbazine (DTIC), also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles also dual topoisomerase-I and II inhibitors like the benzophenazines, XR 11576/MLN 576 and benzopyridoindoles. Such combinations could be given, for example, as intravenous preparations or by oral administration as dependent on the preferred method of administration for the particular agent.

Other further aspects of the invention provide for the treatment of disease ameliorated by the inhibition of PARP, comprising administering to a subject in need of treatment a therapeutically-effective amount of a compound as defined in the first aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with radiotherapy (ionizing radiation) or chemotherapeutic agents.

In further aspects of the present invention, the compounds may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_

000051), RAD51 (NM_002875), RAD51 L1 (NM_002877), RAD51C(NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell*, 115, pp 523-535). HR components are also described in Wood, et al., *Science*, 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science*, 291, 1284-1289 (2001)) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell*, 115, 523-535) or by an epigenetic mechanism such as gene promoter methylation.

BRCA1 and BRCA2 are known tumour suppressors whose wild-type alleles are frequently lost in tumours of heterozygous carriers (Jasin M., *Oncogene*, 21(58), 8981-93 (2002); Tutt, et al., *Trends Mol. Med.*, 8(12), 571-6, (2002)). The association of BRCA1 and/or BRCA2 mutations with breast cancer is well-characterised in the art (Radice, P. J., *Exp. Clin. Cancer Res.*, 21(3 Suppl), 9-12 (2002)). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., *Genet. Test*, 1, 75-83 (1992); Janatova M., et al., *Neoplasma*, 50(4), 246-50 (2003). Determination of amplification of the BRCA2 binding factor EMSY is described in Hughes-Davies, et al., *Cell*, 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

DEFINITIONS

The term "aromatic ring" is used herein in the conventional sense to refer to a cyclic aromatic structure, that is, a cyclic structure having delocalised π-electron orbitals.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl)($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Examples of cycloalkyl groups include, but are not limited to, those derived from Saturated Monocyclic Hydrocarbon Compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

Unsaturated Monocyclic Hydrocarbon Compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

Saturated Polycyclic Hydrocarbon Compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

Unsaturated Polycyclic Hydrocarbon Compounds:
camphene ($C_{10}$), limonene ($C_{10}$), pinene ($C_{10}$);

Polycyclic Hydrocarbon Compounds Having an Aromatic Ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Spiro-$C_{3-7}$ cycloalkyl or heterocyclyl: The term "spiro $C_{3-7}$ cycloalkyl or heterocyclyl" as used herein, refers to a $C_{3-7}$ cycloalkyl or $C_{3-7}$ heterocyclyl ring joined to another ring by a single atom common to both rings.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above alkyl, heterocyclyl, and aryl groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.
Nitro: —NO$_2$.
Cyano (nitrile, carbonitrile): —CN.
Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy(carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amido(carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The cyclic amino groups may be substituted on their ring by any of the substituents defined here, for example carboxy, carboxylate and amido.

Acylamido(acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and R$^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

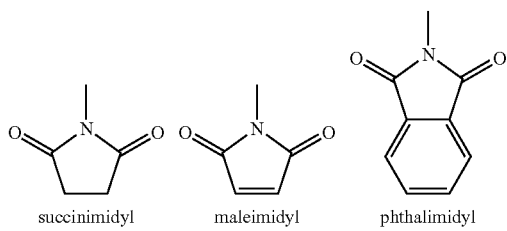

succinimidyl    maleimidyl    phthalimidyl

Ureido: —N(R$^1$)CONR$^2$R$^3$ wherein R$^2$ and R$^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHC(=O)NHPh.

Acyloxy(reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl(tosyl).

Thioamido(thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

EMBODIMENTS

The following particular substituents can apply to each aspect of the present invention, where applicable.

The fused cyclohexene ring may bear one or more substituent groups (R$^H$) at any available ring position. These substituents are selected from halo, nitro, hydroxy, ether, thiol, thioether, amino, $C_{1-7}$ alkyl, $C_{3-20}$ heterocyclyl and $C_{5-20}$ aryl. The fused cyclohexene ring may also bear one or more substituent groups which together form a ring. In particular these may be of formula —(CH$_2$)$_m$— or —O—(CH$_2$)$_p$—O—, where m is 2, 3, 4 or 5 and p is 1, 2 or 3. Particular substituents of interest include, but are not limited to, halo, hydroxy and amino (e.g. NH$_2$).

If the fused cyclohexene ring bears a sole substituent group, the compound may be of the following formula:

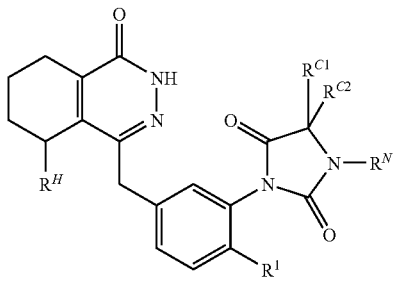

In some embodiments, the cyclohexene ring is unsubstituted.

In some embodiments, $R^1$ is selected from H, Cl and F, or H and F. In some embodiments, $R^1$ is F. In other embodiments, $R^1$ is H.

In some embodiments, $R^{C2}$ is H and $R^{C1}$ is $C_{1-4}$ alkyl. The $C_{1-4}$ alkyl group may be unsubstituted, e.g. methyl, ethyl, propyl. In some embodiments, $R^{C1}$ is methyl.

If the $C_{1-4}$ alkyl (e.g. methyl) is substituted, it may be substituted at its terminus with a carboxy or amido group. The amino substituents of the amido group, together with the N atom to which they are attached, may be cyclic. The cyclic part of the amido group is preferably a $C_{5-7}$ nitrogen containing heterocyclic group, for example, pyrrolidinyl, piperazinyl, homopiperazinyl, piperidinyl, morpholino, all of which may be further substituted, as described above. In particular, substituent groups may include, but are not limited to, hydroxyl, substituted and unsubstituted $C_{1-4}$ alkyl (e.g. methyl, hydroxymethyl, methoxy-ethyl, dimethylamino-ethyl) and $C_{5-7}$ heterocyclyl (e.g. N-piperidinyl, morpholino).

In some embodiments, both $R^{C1}$ and $R^{C2}$ are $C_{1-4}$ alkyl groups. The $C_{1-4}$ alkyl groups may be unsubstituted, e.g. methyl, ethyl, propyl. In some embodiments, $R^{C1}$ and $R^{C2}$ are both methyl.

In some embodiments, $R^N$ is H. In other embodiments, $R^N$ is $C_{1-4}$ alkyl (e.g. methyl, ethyl), which may be unsubstituted or substituted at its terminus with a carboxy, amino or amido group, and additionally an ester group. The amino group or the amino substituents of the amido group, together with the N atom to which they are attached, may be cyclic. The cyclic part of the amino or amido group is preferably a $C_{5-7}$ nitrogen containing heterocyclic group, for example, pyrrolidinyl, piperazinyl, homopiperazinyl, piperidinyl, morpholino, all of which may be further substituted, as described above. In particular, substituent groups may include, but are not limited to, hydroxyl, substituted and unsubstituted $C_{1-4}$ alkyl (e.g. methyl, hydroxymethyl, hydroxyethyl, methoxy-ethyl, dimethylamino-ethyl) and $C_{5-7}$ heterocyclyl (e.g. N-piperidinyl, morpholino).

In some embodiments, $R^{C2}$ is H, $R^{C1}$ is $C_{1-4}$ alkyl (as described above), and $R^N$ is H. In these embodiments, the compound has a chiral centre where $R^{C2}$ and $R^{C1}$ are bound.

The compound may be a racemic mixture of the two stereoisomers, a mixture enriched in one or other of the stereoisomers, or may be one of the stereoisomers substantially isolated from the other.

Where appropriate, the above particular substituents may be taken in combination with each other.

Further aspects of the present invention are the compounds of the examples below (compounds 6, 13, 13a, 13b and 15).

Includes Other Forms

Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair illustrated below:

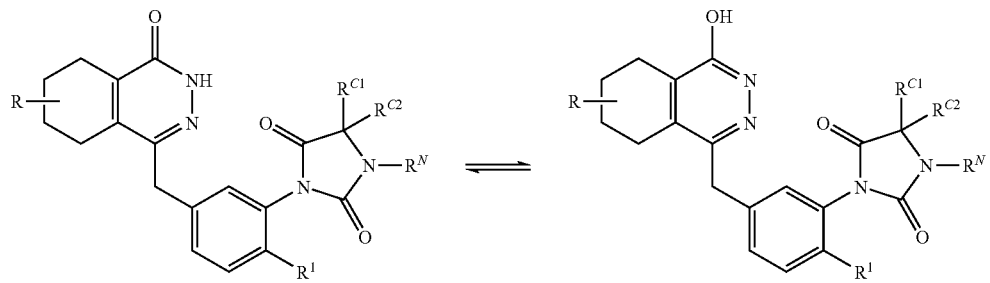

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic and salt forms thereof, for example as discussed below.

Unless otherwise specified, a reference to a particular compound also includes solvates thereof, for example as discussed below.

Unless otherwise specified, a reference to a particular compound also includes prodrugs thereof, for example as discussed below.

Unless otherwise specified, a reference to a particular compound also includes protected forms thereof, for example as discussed below.

Unless otherwise specified, a reference to a particular compound also includes different polymorphic forms thereof, for example as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., "Pharmaceutically Acceptable Salts", *J. Pharm. Sci.*, 66, 1-19 (1977).

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicylic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-20}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleared by phosphotase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

SYNTHESIS

Compounds of formula I of the present invention:

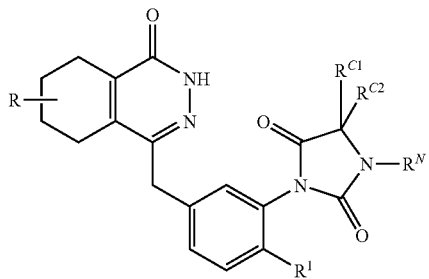

can be synthesized from a precursor of formula 2:

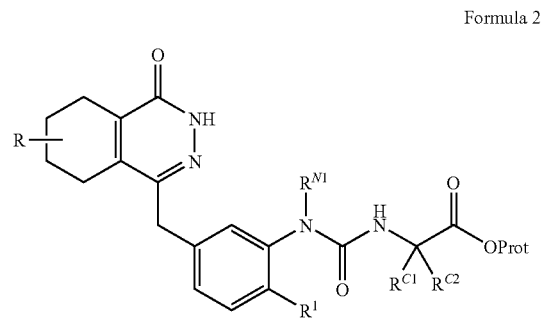

Formula 2 in which R, $R^1$, $R^{N1}$, $R^{C1}$ and $R^{C2}$ are as previously defined and where OProt represents a protected hydroxy group. The various substituent groups shown may be the same as defined for compounds of formula I, or may be protected versions or precursors of those defined groups, such that further transformation is needed to reach the desired compound. The synthesis of the compounds of the invention can proceed by removal of the hydroxy protecting group followed by amide bond formation, using standard techniques, e.g. base catalysation, HBTU coupling.

The compounds of formula 2 can be synthesized by coupling a compound of formula 3 or formula 4:

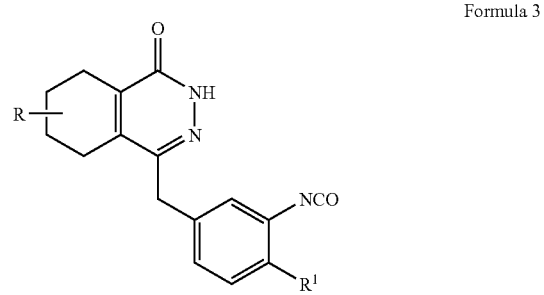

Formula 3

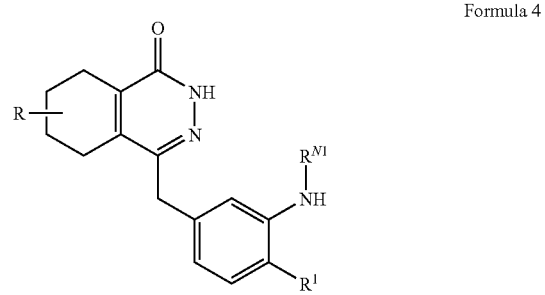

Formula 4 with a compound of formula 5 or 6 respectively:

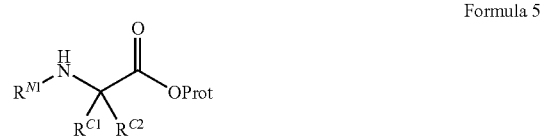

Formula 5

-continued

Formula 6

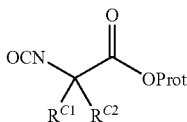

in which R, $R^1$, $R^{N1}$, $R^{C1}$, $R^{C2}$ and OProt are as previously defined.

The urea bond formation reaction is carried out under standard conditions. Compounds of formulae 5 and 6 may be synthesized according to known methods (see, e.g. examples of 2007/045877).

Compounds of Formula 4, wherein $R^{N1}$ is H may be synthesized from a compound of formula 7:

Formula 7

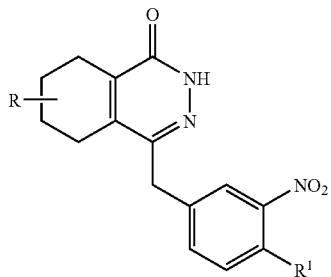

in which R and $R^1$ are as previously defined, by reduction of the nitro group. This may be done, for example, using iron powder and ammonium chloride.

Compounds of formula 7 may be synthesized from compounds of formula 8:

Formula 8

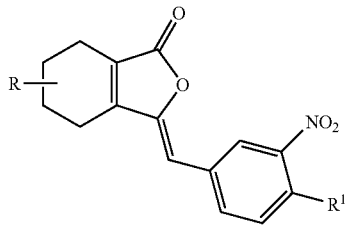

in which R and $R^1$ are as previously defined, by reaction with a source of hydrazine, for example hydrazine hydrate, at a temperature in the range of 0° C. to the boiling point of the solvent used.

Compounds of formula 8 may be synthesized from compounds of formula 9:

Formula 9

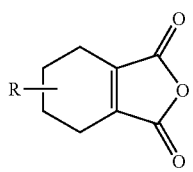

in which R is as previously defined, by reaction with a compound of formula 10:

Formula 10

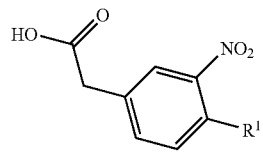

in which $R^1$ is as previously defined, in the presence of sodium acetate at high temperature (e.g. about 240° C.).

Compounds of formula 2:

Formula 2

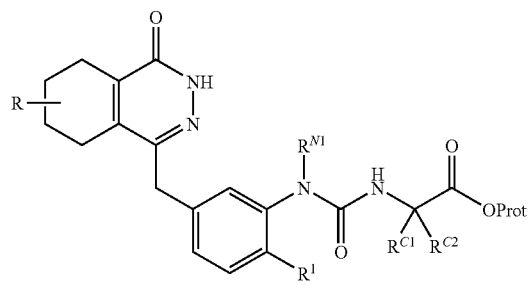

in which R, $R^1$, $R^{C1}$, $R^{C2}$ and OProt are as previously defined and in which $R^{N1}$ is H may also be synthesized from a compound of formula 11:

Formula 11

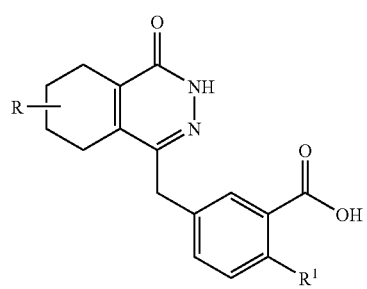

in which R and $R^1$ are as previously defined, by treatment with a tertiary amine (e.g triethylamine) followed by reaction with Formula 12

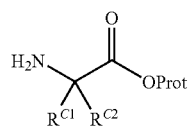

in which $R^{C1}$, $R^{C2}$ and OProt are as previously defined, simultaneously with an azide (e.g. diphenylphosphinic azide).

Compounds of Formula 11 may be synthesised by reaction of a compound of Formula 13:

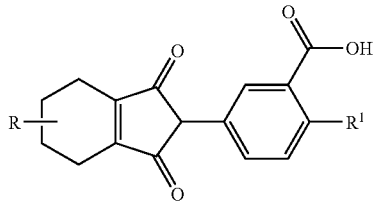

Formula 13 in which R and R$^1$ are as previously defined, or a compound of Formula 14:

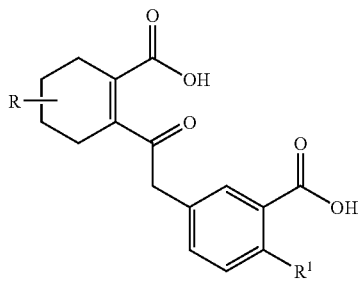

Formula 14 in which R and R$^1$ are as previously defined, or a mixture of a compound of Formula 13 and a compound of Formula 14, with a source of hydrazine, for example hydrazine hydrate, optionally in the presence of a base, for example triethylamine, optionally in the presence of a solvent, for example industrial methylated spirit, at a temperature in the range of 0° C. to the boiling point of the solvent used.

Compounds of Formula 13 or Formula 14, or mixtures thereof, may be synthesised by reaction of a compound of Formula 15:

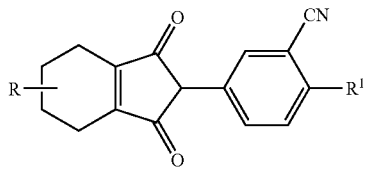

Formula 15 in which R and R$^1$ are as previously defined, with a reagent capable of hydrolysing a nitrile moiety, for example sodium hydroxide, in the presence of a solvent, for example water, at a temperature in the range of 0° C. to the boiling point of the solvent used.

Compounds of Formula 15 may be synthesised by reaction of a compound of Formula 16:

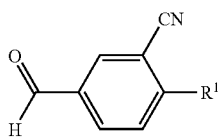

Formula 16 in which R$^1$ is as previously defined, with a compound of Formula 17:

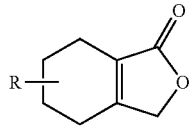

Formula 17 in which R is as previously defined, in the presence of a base, for example sodium methoxide, in a solvent, for example methanol, optionally in the presence of a water scavenger, for example ethyl propionate, at a temperature in the range of 0° C. to the boiling point of the solvent used.

Compounds of Formula 1 may also be synthesised by reaction of a compound of Formula 18:

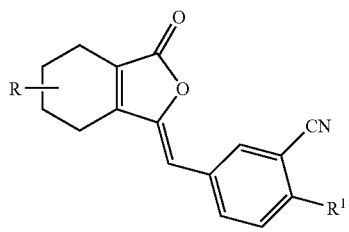

Formula 18 in which R and R$^1$ are as previously defined, with a reagent capable of hydrolysing a nitrile moiety, for example sodium hydroxide, in the presence of a solvent, for example water, at a temperature in the range of 0° C. to the boiling point of the solvent used, followed by reaction of the resulting intermediate with a source of hydrazine, for example hydrazine hydrate, at a temperature in the range of 0° C. to the boiling point of the solvent used.

Compounds of Formula 18 may be synthesised by reaction of a compound of Formula 19:

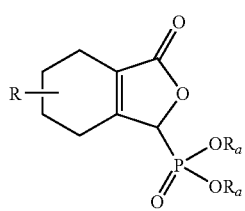

Formula 19 in which R is as previously defined and R$_a$ is a C$_{1-4}$ alkyl group, with a compound of Formula 6, in the presence of a base, for example triethylamine or lithium hexamethyldisilazide, in the presence of a solvent, for example tetrahydrofuran, at a temperature in the range of −80° C. to the boiling point of the solvent used.

Compounds of Formula 19 may be synthesised by methods analogous to those described in WO 02/26576.

Compounds of Formula 11 may also be synthesised by methods analogous to those described above in which the nitrile moiety in all Formulae is replaced by other moieties capable of generating a carboxylic acid, for example ester or carboxamide moieties, or a precursor to the nitrile (e.g. bromo).

Use

The present invention provides active compounds, specifically, active in inhibiting the activity of PARP.

The term "active" as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect", the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

Active compounds may also be used as cell culture additives to inhibit PARP, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer=s Solution, or Lactated Ringer=s Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

General Experimental Methods

Preparative HPLC

| Instrument: | Waters ZMD LC-MS system No. LD352 operating in Electrospray ionisation mode. |
|---|---|
| Mobile Phase A: | 0.1% Formic acid in water |
| Mobile Phase B: | 0.1% Formic acid in acetonitrile |
| Column: | Genesis C18 4 μm 50 × 4.6 mm |

| Gradient: | Time (mins.) | % B |
|---|---|---|
| | 0 | 5 |
| | 7 | 95 |
| | 9 | 95 |
| | 9.5 | 5 |
| | 13 | 5 |

| Flow rate: | 1.0 ml/min. |
|---|---|
| PDA Scan range: | 210-400 nm. |

Example 1

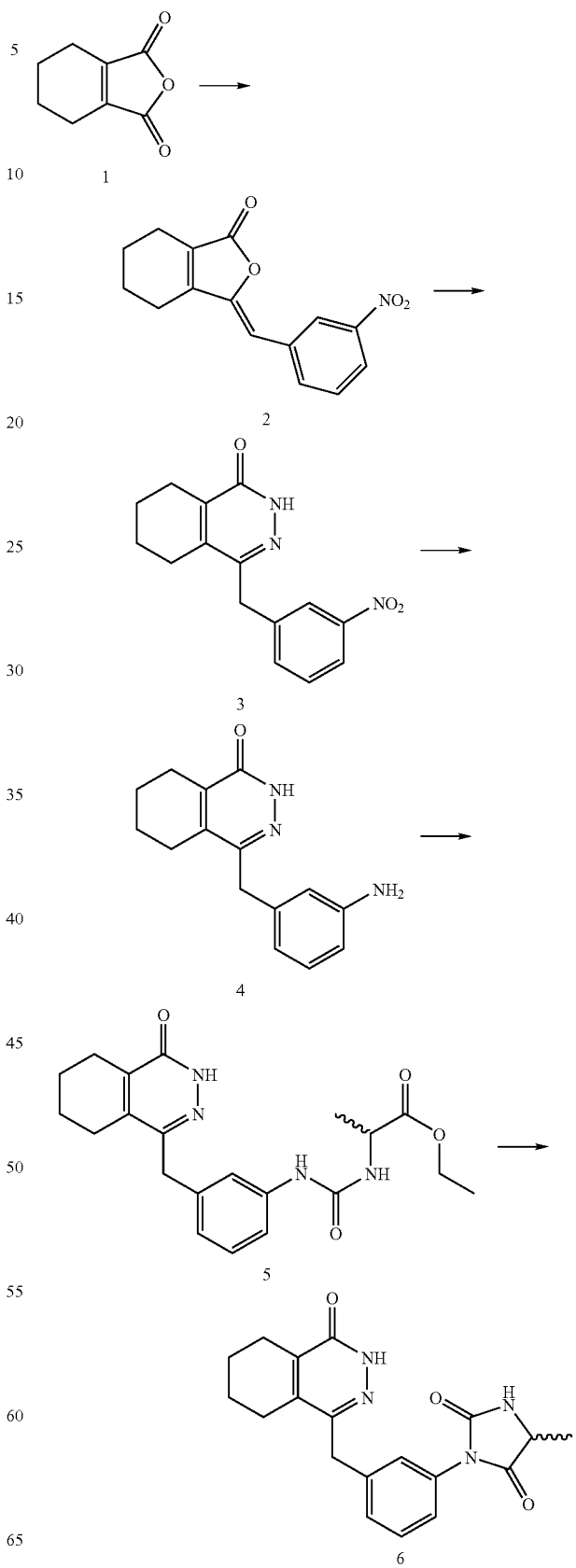

(a) 3-(3-Nitro-benzylidene)-4,5,6,7-tetrahydro-3H-isobenzofuran-1-one (2)

4,5,6,7-Tetrahydro-isobenzofuran-1,3-dione (1) (2.50 g, 16.4 mmol) and 3-nitro phenyl acetic acid (2.72 g, 15.0 mmol) were heated in the presence of sodium acetate (60.0 mg, 0.750 mmol) to 240° C. using a 'Wood's Alloy' bath. Once the reaction had reached 240° C. an additional amount of sodium acetate (60.1 mg, 0.750 mmol) was added. The reaction mixture was then heated for a further 45 minutes and then cooled to 80° C. Ethanol (20 ml) was added to the thick gum and the mixture slurried for 30 minutes. The resulting suspension was cooled to ambient temperature and filtered. The solid was further washed with additional cold ethanol (2×5 ml) and dried to afford the desired product as a mixture of geometric isomers. Main peak in LC-MS, (2.48 g) and was taken through crude; m/z (LC-MS, ESP), RT=4.48 mins (no ionization observed).

(b) 3-(3-Methyl-benzylidene)-4,5,6,7-tetrahydro-3H-isobenzofuran-1-one (3)

A suspension of 3-(3-nitro-benzylidene)-4,5,6,7-tetrahydro-3H-isobenzofuran-1-one (2) (2.48 g, 13.9 mmol) in water (25 ml), was treated with hydrazine hydrate (1.7 ml, 34.0 mmol) dropwise and then heated to 100° C. for 16 hours. The mixture was cooled to approximately 5° C. and the resultant suspension filtered and washed with water (5 ml) and diethyl ether (2×5 ml). The solid was then dried in a vacuum oven overnight. Main peak in LC-MS, (2.48 g, 84% purity) and required no further purification; m/z (LC-MS, ESP), RT=3.55 mins (M+H 285).

(c) 4-(3-Amino-benzyl)-5,6,7,8-tetrahydro-2H-phthalazin-1-one (4)

To a suspension of 3-(3-methyl-benzylidene)-4,5,6,7-tetrahydro-3H-isobenzofuran-1-one (3) (2.48 g, 8.720 mmol, in ethanol (50 ml) and water (50 ml) was added, in one portion, iron powder (0.96 g, 17.2 mmol), ammonium chloride (450 mg, 8.720 mmol). The reaction was heated to 80° C. for 3 hours and then cooled to room temperature. The dark brown suspension was the filtered and plug washed through celite with ethanol (2×25 ml). The filtrate was concentrated in vacuo to afford a pale brown foam. Main peak in LC-MS, (1.69 g, 97% purity) and required no further purification; m/z (LC-MS, ESP), RT=2.75 mins (M+H 256).

(d) 2-{3-[3-(4-Oxo-3,4,5,6,7,8-hexahydro-phthalazin-1-ylmethyl)-phenyl]-ureido}-propionic acid ethyl ester (5)

To a solution of 4-(3-amino-benzyl)-5,6,7,8-tetrahydro-2H-phthalazin-1-one (4) (0.472 mg, 1.850 mmol) in dry THF (25 ml) was added a solution of ethyl 2-isocyanopropionate (266 mg, 1.850 mmol) in 2 ml of THF. The resultant solution was then stirred for 4 hours and then concentrated in vacuo to afford a brown oil. The crude oil was subjected to flash chromatography eluent 4:1, hexane:ethyl acetate. (Rf=0.14 neat ethyl acetate). Main peak in LC-MS, (7.20 g, 98% purity); m/z (LC-MS, ESP), RT=3.20 mins (M+H 389.4).

(e) 5-Methyl-3-[3-(4-oxo-3,4,5,6,7,8-hexahydrophthalazin-1-ylmethyl)-phenyl]-imidazolidine-2,4-dione (6)

To a solution of 2-{3-[3-(4-oxo-3,4,5,6,7,8-hexahydro-phthalazin-1-ylmethyl)-phenyl]-ureido}-propionic acid ethyl ester (5) (0.715 g, 1.80 mmol) in dry DMA (2 ml) was added finely powdered sodium hydroxide (71 mg, 1.80 mmol). The reaction mixture was then immersed in a preheated oil bath at 50° C. and heated for 10 minutes before being quenched by addition of HCl (1N, 0.5 ml). The reaction mixture was then concentrated to dryness in vacuo. The crude oil was subjected to flash chromatography eluent 4:1, hexane:ethyl acetate (Rf=0.18, neat ethyl acetate). Main peak in LC-MS, (0.25 g, 95% purity); $^1$H NMR (300 MHz, D$_6$ DMSO, δ ppm 12.61 (s, 1H), 8.41 (s, 1H), 7.40 (dd, J=11.46, 4.58 Hz, 1H), 7.29-7.12 (m, 2H), 4.32-4.15 (m, 1H), 3.94 (s, 2H), 2.46 (m, 4H), 1.61 (s, 4H), 1.34 (d, J=6.94 Hz, 3H). M/z (LC-MS, ESP), RT=3.04 mins (M+H 353.2).

Example 2

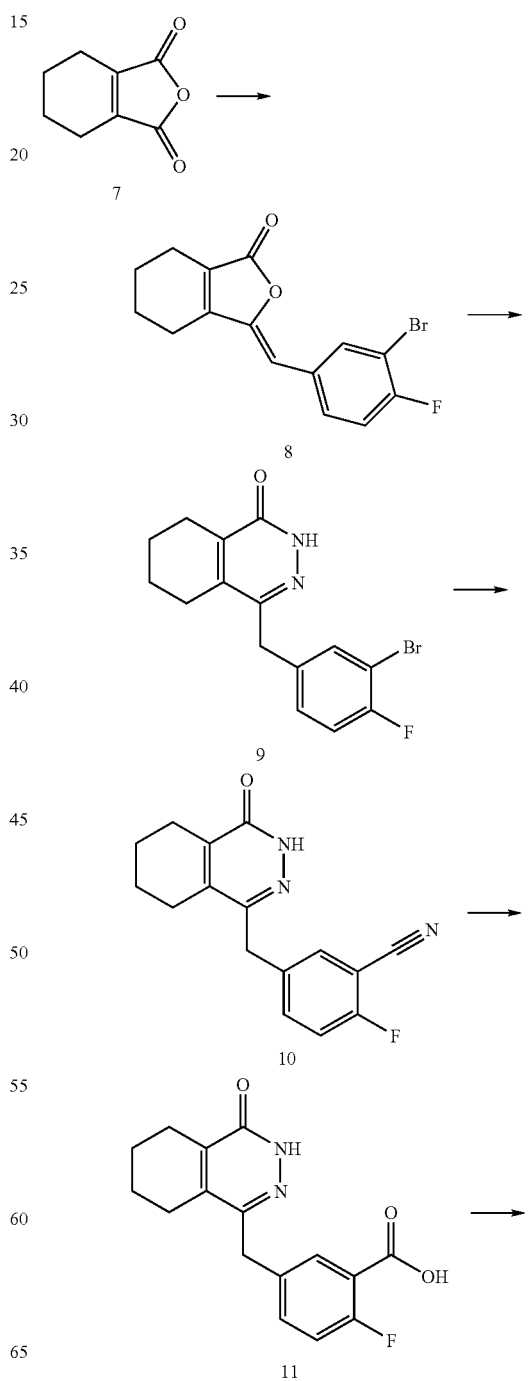

-continued

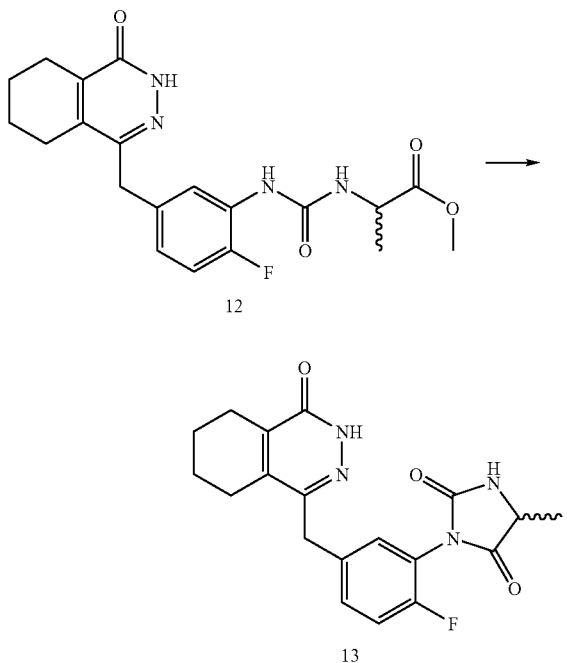

(a) 3-(3-Bromo-4-fluoro-benzylidene)-4,5,6,7-tetrahydro-3H-isobenzofuran-1-one (8)

4,5,6,7-tetrahydro-isobenzofuran-1,3-dione (7) (16.7 g, 109.7 mmol) and 3-bromo-4-fluorophenylacetic acid (15.0 g, 64.37 mmol) were heated in the presence of sodium acetate (0.259 g, 3.160 mmol) to 210° C. using a 'Wood's Alloy' bath for 4.5 hours. The reaction mixture was then poured into a crucible and cooled to give a crystalline solid. The solid was ground with a mortar and pestle and triturated with ethanol (20 ml). The resultant suspension was then filtered and washed with further ethanol (10 ml). The solid was then dried to afford the desired product as a mixture of geometric isomers. Main peak in LC-MS, (20.78 g, 94% purity) and required no further purification; m/z (LC-MS, ESP), RT=4.74 mins (no ionization observed).

(b) 4-(3-Bromo-4-fluoro-benzyl)-5,6,7,8-tetrahydro-2H-phthalazin-1-one (9)

To 3-(3-bromo-4-fluoro-benzylidene)-4,5,6,7-tetrahydro-3H-isobenzofuran-1-one (8) (cis 1 trans mixture) (20.78 g, 64.3 mmol) suspended in water (150 ml) was added hydrazine hydrate (12.5 ml, 257.2 mmol). The reaction was heated to 85° C. for 18 hours and then cooled to room temperature. A beige suspension was isolated by filtration and washed with water (1×50 ml), hexane (1×50 ml), and ether (1×25 ml) before being dried overnight in a vacuum oven. Main peak in LC-MS, (19.1 g, 91% purity) and required no further purification; m/z (LC-MS, ESP), RT=3.92 mins (M+H 337 & 339).

(c) 2-Fluoro-5-(4-oxo-3,4,5,6,7,8-hexahydro-phthalazin-1-ylmethyl)-benzonitrile (10)

To a solution of 4-(3-bromo-4-fluoro-benzyl)-5,6,7,8-tetrahydro-2H-phthalazin-1-one (9) (9.53 g, 28.2 mmol), in dry DMF (95 ml) was added copper (I) cyanide (3.5 g, 42.3 mmol) in one portion. The mixture was heated to 160° C. for 18 hours. The reaction was then cooled and filtered through celite and washed though with methanol (30 ml). The filtrate was concentrated in vacuo to afford a brown oil. Main peak in LC-MS, (8.01 g, 66% purity) and was taken through crude to the next transformation; m/z (LC-MS, ESP), RT=3.50 mins (M+H 284.3).

(d) 2-Fluoro-5-(4-oxo-3,4,5,6,7,8-hexahydro-phthalazin-1-ylmethyl)-benzoic acid (11)

Crude 2-fluoro-5-(4-oxo-3,4,5,6,7,8-hexahydro-phthalazin-1-ylmethyl)benzonitrile (10) (9.9 g, 34.9 mmol) was suspended in water (245 ml) and treated with sodium hydroxide (6.98 g, 174 mmol). The mixture was heated to 60° C. for 18 hours. The reaction was then cooled to 5° C. and concentrated sulfuric acid added dropwise until a precipitate formed (ca 10 ml, pH2). The suspension was stirred for 10 minutes at 5° C. and filtered. The solid isolated was washed with water (2×8 ml) and triturated with DCM (20 ml) before being dried. Single peak in LC-MS, (4.48 g, 98% purity) and was taken through to the next without any further purification; m/z (LC-MS, ESN), RT=1.96 mins (M−H 301.3).

(e) 2-{3-[2-Fluoro-5-(4-oxo-3,4,5,6,7,8-hexahydro-phthalazin-1-ylmethyl)-phenyl]-ureido}-propionic Acid Methyl Ester (12)

To a suspension of 2-fluoro-5-(4-oxo-3,4,5,6,7,8-hexahydro-phthalazin-1-ylmethyl)benzoic acid (11) (0.50 g, 1.650 mmol), in acetonitrile (2.5 ml) was added triethylamine (0.46 ml, 3.31 mmol) the suspension dissolved to afford a brown solution which was subsequently heated to 85° C. D/L alanine methyl ester hydrochloride (2.30 g, 1.650 mmol) dissolved in acetonitrile (5 ml) and N-methylpyrrolidinone (0.5 ml) was added simultaneously to the reaction mixture with diphenylphosphinic azide (0.357 ml, 1.650 mmol). After 40 minutes of heating the reaction mixture was cooled to ambient temperature and concentrated to vacuo. The crude oil was then subjected to flash chromatography, eluent hexane/ethyl acetate, 7:13 ($R_f$=0.14). Single peak in LC-MS, (0.67 g, 98% purity); m/z (LC-MS, ESP), RT=3.37 mins (M+H 403.2).

(f) 3-[2-Fluoro-5-(4-oxo-3,4,5,6,7,8-hexahydro-phthalazin-1-ylmethyl)-phenyl]-5-methylimidazolidine-2,4-dione (13)

To a solution of 2-{3-[2-fluoro-5-(4-oxo-3,4,5,6,7,8-hexahydro-phthalazin-1-ylmethyl)-phenyl]-ureido}-propionic acid methyl ester (12) (0.425 g, 1.053 mmol), in dry DMA (5 ml), was added ground sodium hydroxide (0.433 mg, 1.053 mmol) in one portion. The reaction mixture was then placed in a preheated oil bath at 50° C. for 10 minutes and neutralised by addition of HCl (2N, ca 1 ml). The mixture was then concentrated to dryness and subjected to flash chromatography, eluent neat ethyl acetate ($R_f$=0.15). Single peak in LC-MS, (0.457 g, 99% purity); $^1$H NMR (300 MHz, $D_6$ DMSO) δ ppm 12.61 (s, 1H), 8.51 (s, 1H), 7.40-7.15 (m, 3H), 4.32 (m, 1H), 3.93 (s, 2H), 2.46 (m, 4H), 1.63 (s, 4H), 1.35 (d, J=6.94 Hz, 3H). M/z (LC-MS, ESP), RT=3.28 mins (M+H 371.1).

Example 3

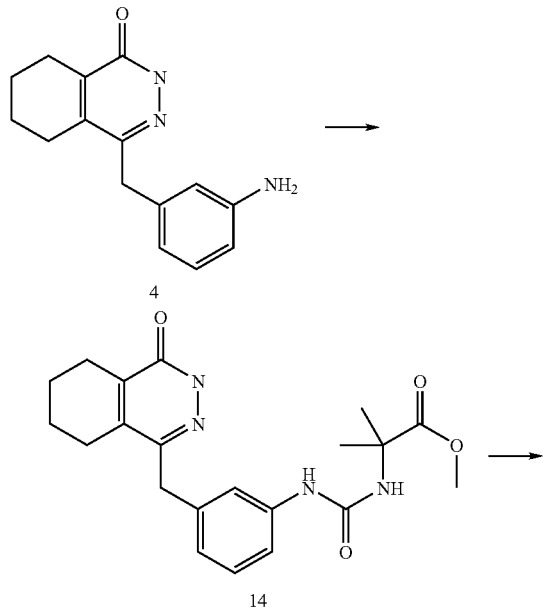

(a) Methyl 2-methyl-2-[[3-[(4-oxo-5,6,7,8-tetrahydro-3H-phthalazin-1-yl)methyl]phenyl]carbamoylamino]propanoate (14)

To a solution of 4-(3-amino-benzyl)-5,6,7,8-tetrahydro-2H-phthalazin-1-one (4) (50 mg, 0.195 mmol) in dry DCM (10 ml) was added 2-isocyanato-2-methyl-propionic acid methyl ester (60 mg, 0.428 mmol). The resulting solution was stirred for 2 days, washed with water (3×10 ml), dried over sodium sulphate and concentrated in vacuo to yield a semi-crystalline solid (44 mg).

(b) 5,5-dimethyl-3-[3-[(4-oxo-5,6,7,8-tetrahydro-3H-phthalazin-1-yl)methyl]phenyl]imidazolidine-2,4-dione (15)

To a solution of methyl 2-methyl-2-[[3-[(4-oxo-5,6,7,8-tetrahydro-3H-phthalazin-1-yl)methyl]phenyl]carbamoylamino]propanoate (14) (44 mg, 0.11 mmol) in dry DMF (2 mL) was added finely powdered sodium hydroxide (4 mg, 0.072 mmol). The reaction mixture was immersed in a preheated oil bath at 50° C. for 5 hours, before being neutralized by addition of 1M HCl The desired product was isolated from the resultant solution by preparative chromatography to yield a solid (3.6 mg, 98% purity). M/z (LC-MS, ESP), RT=7.69 mins (M+H 367.1).

Example 4

A solution of 3-[2-fluoro-5-(4-oxo-3,4,5,6,7,8-hexahydro-phthalazin-1-ylmethyl)-phenyl]-5R/S-methylimidazolidine-2,4-dione (13) (250 mg, 0.67 mmol) in isopropyl alcohol (12 mL) and hexane (6 mL) was passed through Merck 50 mm 20 μm Chiralcel OD column attached to a Gilson Prep (200 ml head) system, flow rate (40 mL, min) isocratic eluent of Hexane:Iso propyl alcohol 50/50. The fractions were monitored at 270 nM & 230 nM. Two components were collected and concentrated in vacuo to afford:
RT=15.32-19.56 mins fraction A (125 mg)
RT=33.46-41.90 mins fraction B (125 mg)
Analysis Conditions

| Instrument | Gilson Prep (200 ml heads) |
|---|---|
| Column | Merck 50 mm 20 μm Chiralcel OD - No HE001 Packed 21-01-03 |
| Eluent | iso-Hexane/IPA 50/50 |
| Flow | 40 ml/min |
| Wavelength | 270, 230 nm |
| Sample Conc | 18 mg/ml (250 mg in 8 ml IPA then 6 ml mobile phase) |
| Injection volume | 14 ml (250 mg) |
| Run Time | 50 min |

The compounds isolated were:

| Compound | Enantiomeric Excess | RT on Chiracel Column (mins) | M + H |
|---|---|---|---|
| 13a | >98% | 33.46 – 41.90 | 371.2 |
| 13b | >98% | 15.32 – 19.56 | 371.2 |

Example 5

Inhibitory Action

In order to assess the inhibitory action of the compounds, the following assay was used to determine $IC_{50}$ values.

Mammalian PARP, isolated from Hela cell nuclear extract, was incubated with Z-buffer (25 mM Hepes (Sigma); 12.5 mM $MgCl_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 µM, with the DMSO being at a final concentration of 1% per well. The total assay volume per well was 4 µl.

After 10 minutes incubation at 30° C. the reactions were initiated by the addition of a 10 µl reaction mixture, containing NAD (5 µM), $^3$H-NAD and 30mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 µl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{\left(\begin{array}{c}cpm \text{ of unknowns} - \\ \text{mean negative } cpm\end{array}\right)}{\left(\begin{array}{c}\text{mean positive } cpm - \\ \text{mean } neagative \text{ } cpm\end{array}\right)}\right)$$

$IC_{50}$ values (the concentration at which 50% of the enzyme activity is inhibited) were calculated, which are determined over a range of different concentrations, normally from 10 µM down to 0.001 µM. Such $IC_{50}$ values are used as comparative values to identify increased compound potencies.

Compound 6 had a mean $IC_{50}$ of 5 nM and compound 13 had a mean $IC_{50}$ of 4 nM.

Compound 13a had a mean $IC_{50}$ of 3 nM, and compound 13b had a mean $IC_{50}$ of 5 nM.

Compound 15 had a mean $IC_{50}$ of 28 nM.

Potentiation Factor

The Potentiation Factor ($PF_{50}$) for compounds is calculated as a ratio of the $IC_{50}$ of control cell growth divided by the $IC_{50}$ of cell growth+PARP inhibitor. Growth inhibition curves for both control and compound treated cells are in the presence of the alkylating agent methyl methanesulfonate (MMS). The test compounds were used at a fixed concentration of 0.2 micromolar. The concentrations of MMS were over a range from 0 to 10 µg/ml.

Cell growth was assessed using the sulforhodamine B (SRB) assay (Skehan, P., et al., (1990) New calorimetric cytotoxicity assay for anticancer-drug screening. J. Natl. Cancer Inst. 82, 1107-1112). 2,000 HeLa cells were seeded into each well of a flat-bottomed 96-well microtiter plate in a volume of 100 µl and incubated for 6 hours at 37° C. Cells were either replaced with media alone or with media containing PARP inhibitor at a final concentration of 0.5, 1 or 5 µM. Cells were allowed to grow for a further 1 hour before the addition of MMS at a range of concentrations (typically 0, 1, 2, 3, 5, 7 and 10 µg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The media was then removed and the cells fixed with 100 µl of ice cold 10% (w/v) trichloroacetic acid. The plates were incubated at 4° C. for 20 minutes and then washed four times with water. Each well of cells was then stained with 100 µl of 0.4% (w/v) SRB in 1% acetic acid for 20 minutes before washing four times with 1% acetic acid. Plates were then dried for 2 hours at room temperature. The dye from the stained cells was solubilized by the addition of 100 µl of 10 mM Tris Base into each well. Plates were gently shaken and left at room temperature for 30 minutes before measuring the optical density at 564 nM on a Microquant microtiter plate reader.

Compound 6 had a mean $PF_{50}$ at 200 nM of 20 and compound 13 had a mean $PF_{50}$ at 200 nM of 57.

Compound 13a had a mean $PF_{50}$ at 30 nM of 25, and compound 13b had a mean $PF_{50}$ at 30 nM of 9.

Compound 15 had a mean $PF_{50}$ at 200 nM of 2.

Solubility Assay

A typical assay that may be used to assess the solubility of the compounds of the present invention is as follows. The solubility of the compound is assessed in water and phosphate-buffered saline (pbs) at pH 7.4. The samples are all allowed to equilibrate in the solvent (with shaking) for 20 hours at room temperature. After that period, the samples will be visually examined to determine the presence/absence of un-dissolved solid. The samples will be centrifuged or filtered as necessary to remove insoluble material, and the solution analysed to determine solubility of the DS, diluting both aqueous and DMSO samples to a similar concentration with DMSO. The area of the peak obtained by HPLC (using the diode array detector) from the sample will be compared to the area of the peak from the DMSO solution (diluted to the same concentration as the sample) and quantified taking into account the weight of sample taken for initial dissolution. The assumption is made that the sample will be completely soluble in DMSO at the levels used for testing.

Comparing the ratio of the peak areas, and knowing the concentration of the original samples, the solubility may be calculated.

Preparation of Samples

About 1 mg of the sample is weighed accurately into a 4-ml glass vial and exactly 1.0 ml of water, aqueous buffer or DMSO, is added to it by pipette. Each vial is ultrasonicated for up to 2 minutes to assist solublisation of the solid. The samples are retained at room temperature for 20 hours, shaking on an orbital shaker. The vials are examined after this period to determine the presence/absence of un-dissolved solid. The samples should be centrifuged, or filtered through a 0.45 µm filter, to remove insoluble material if necessary, and the filtrate analysed to determine concentration of the compound in solution, after diluting all samples as appropriate with DMSO. 20 µl is injected onto the HPLC using the method shown below, injecting all samples in duplicate. The maximum solubility that can be determined using this method is nominally 1.0 mg/ml, the weight taken divided by the volume of solvent used.

Analytical Techniques

The samples are subjected to LC/MS using a Waters Micromass ZQ instrument (or equivalent) with test parameters typically as follows.

Waters Micromass ZQ in positive ion mode.

Scanning from m/z 100 to 800

Mobile phase A—0.1% aqueous formic acid

Mobile phase B—0.1% formic acid in Acetonitrile

Column—Jones Chromatography Genesis 4μ C18 column, 4.6×50 mm
Flow rate 2.0 ml/min
Injection volume 30 μl injection into a 20 μl loop.
Gradient—starting at 95% A/5% B, rising to 95% B after 4 minutes, holding there for four minutes, then back to the starting conditions. (This may be modified if necessary to obtain better separation of peaks).
PDA detection scanning from 210 to 400 nm
Quantification of Samples Initial examination of the sample vials containing the aqueous dilution indicates whether or not the compound is soluble in that buffer at that concentration. If it is not soluble, this should be reflected in the concentration obtained in solution by HPLC/MS. If the solution is clear, then the concentration in aqueous solvent should be similar to that in DMSO, unless degradation of the compound has occurred; this should be visible on the chromatogram.

The assumption is made that the samples will be completely soluble in DMSO, therefore the peak size obtained from that sample will reflect 100% solubility. Assuming that the dilutions of all samples have been the same, then solubility in mg/ml=(area from pbs solution/area from DMSO solution)×(original weight in DMSO solution/dilution).

Compound 6 had a solubility in water of 0.5 mg/ml and compound 13 had a solubility in water of 0.9 mg/ml. Compound 15 had a solubility in water of 0.105 mg/ml.

VC8 Assay

In order to assess the growth inhibitory action of compounds on BRCA2 deficient (VC8–hamster line) and BRAC2 complemented (VC8+BAC) cells the following assay was used to determine $GI_{50}$ values.

500 VC8 cells or 200 VC8+BAC cells were seeded into each well of a flat-bottomed 96-well microtiter plate in a volume of 90 μl and incubated for 4-6 hours at 37° C. All compounds were diluted in media (Dulbecco's Modified Eagle's Medium (DMEM), 10% Fetal Bovine Serum, Penicillin/Sretptomycin/Glutamine) and added to the cells at final concentrations of between 0 and 300 nM.

Cells were left for a further 48 hours before replacing the media with fresh media (no compound) and allowing the cells to grow for a total of 120 hours at 37° C. The medium was then removed and the cells fixed with 50 μl of ice cold 10% (w/v) tricholoracetic acid. The plates were incubated at 4° C. for 30 minutes and then washed three times with water. Each well of cells was then stained with 50 μl of 0.4% (w/v) sulforhodamine B (SRB) in 1% acetic acid for 15 minutes before washing three times with 1% acetic acid. Plates were then dried for 2 hours at room temperature. The dye from the stained cells was solubilised by the addition of 100 μl of 10 mM Tris Base into each well. Plates were then shaken and the optical density at 564 nM was measured on a Microquant microtiter plate reader.

The $GI_{50}$ is calculated as the μM concentration of compound required to inhibit 50% of cell growth.

Compound 13 had a mean $GI_{50}$ for VC8 of 0.0105 μM and a $GI_{50}$ for VC8+BAC of 28.97 μM.

The invention claimed is:

1. A compound of the formula:

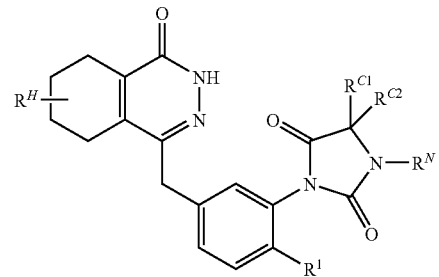

wherein:
$R^1$ is selected from H and halo;
$R^N$ is H; and
$R^{C1}$ and $R^{C2}$ are independently selected from H and R, where R is $C_{1-4}$ alkyl.

2. The compound according to claim 1, wherein $R^1$ is selected from H, Cl and F.

3. The compound according to claim 2, wherein $R^1$ is selected from H and F.

4. The compound according to claim 1, wherein $R^{C2}$ is H and $R^{C1}$ is a $C_{1-4}$ alkyl group.

5. The compound according to claim 4, wherein $R^{C1}$ is methyl.

6. A pharmaceutical composition comprising a compound according to any one of claims 1 and 2 to 5 and a pharmaceutically acceptable carrier or diluent.

* * * * *